United States Patent [19]

Jakobs

[11] 4,202,629
[45] May 13, 1980

[54] APPARATUS FOR THE DETERMINATION OF THE PARTICLE SIZE DISTRIBUTION OF A GRANULAR MATERIAL

[75] Inventor: Willy Jakobs, Cologne, Fed. Rep. of Germany

[73] Assignee: Klöckner-Humboldt-Deutz Aktiengesellschaft, Fed. Rep. of Germany

[21] Appl. No.: 922,338

[22] Filed: Jul. 6, 1978

[30] Foreign Application Priority Data

Jul. 7, 1977 [DE] Fed. Rep. of Germany ....... 2730731

[51] Int. Cl.² .............................................. G01N 21/26
[52] U.S. Cl. ..................... 356/335; 250/573; 356/439
[58] Field of Search ...................... 356/335, 438, 439; 250/573; 73/432 PS

[56] References Cited

U.S. PATENT DOCUMENTS

| | | | |
|---|---|---|---|
| 3,597,084 | 8/1971 | Pagano | 250/573 X |
| 3,739,180 | 6/1973 | Carlson | 356/335 X |
| 3,952,207 | 4/1976 | Leschonski et al. | 250/573 |

*Primary Examiner*—F. L. Evans
*Assistant Examiner*—Matthew W. Koren
*Attorney, Agent, or Firm*—Hill, Van Santen, Steadman, Chiara & Simpson

[57] ABSTRACT

An apparatus is disclosed for the determination of particle size distribution of a granular material within a measuring channel. The measuring channel has radiation permeable side walls and a granular material is spread out through the measuring channel by a sifting air current in accordance with grain size. A scanning apparatus is movable external to the measuring channel and includes a frame on which is mounted a radiation transmitter and a radiation receiver lying opposite the transmitter. A measuring beam from the transmitter scans through a measuring zone of the measuring channel. The measuring frame is of closed-loop construction and surrounds the measurement channel. With such construction, the frame is not subject to vibration particularly when reciprocated in order to cause scanning movement of the measuring beam.

11 Claims, 2 Drawing Figures

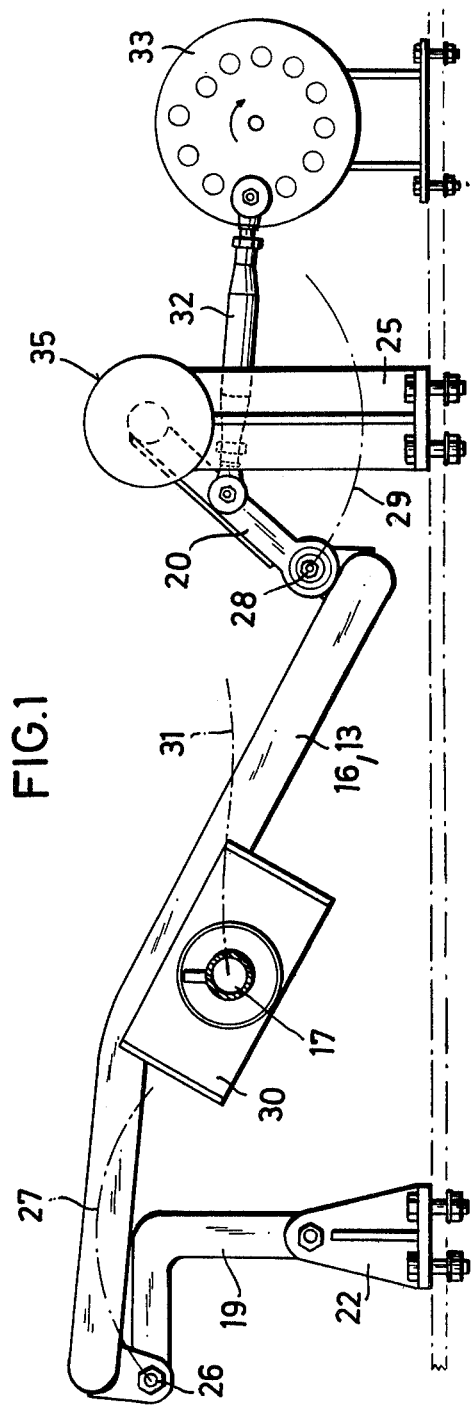

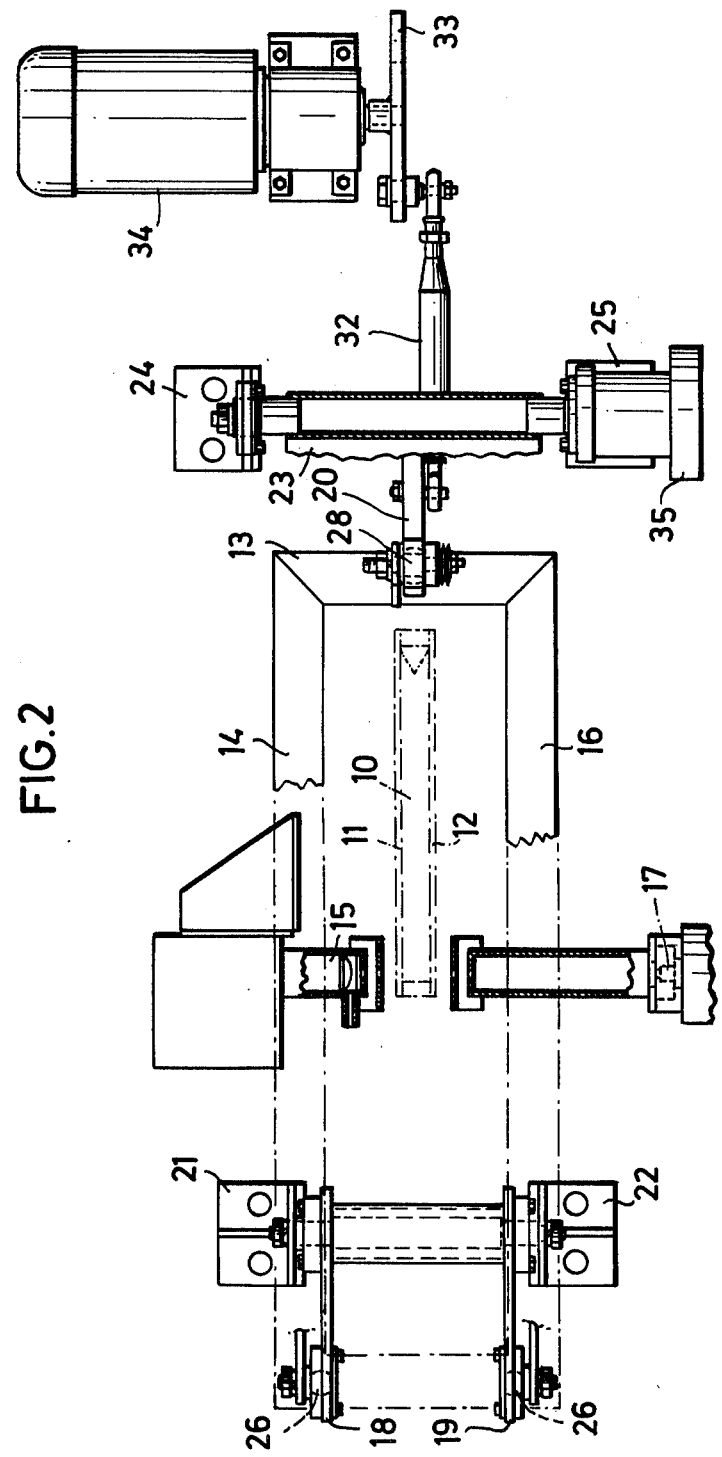

APPARATUS FOR THE DETERMINATION OF THE PARTICLE SIZE DISTRIBUTION OF A GRANULAR MATERIAL

BACKGROUND OF THE INVENTION

The invention relates to an apparatus for the determination of the particle size distribution of a granular material by use of a measuring channel equipped with radiation permeable side walls. The granular material is introduced into the measuring channel and, by means of a sifting air current, is fanned out according to the granular size. A scanning apparatus movable outside of the measuring channel is provided consisting of a radiation transmitter and a radiation receiver disposed opposite the transmitter. A measuring beam of this scanning apparatus scans the material blower in a measuring zone lying transversely to the measuring channel.

In a known apparatus of this type (German Pat. No. 2,304,879), the measuring channel consists of a vertically standing, rectangular housing which has flowing therethrough from top to bottom with constant speed a sifting air current into which the granular material to be analyzed is introduced perpendicularly thereto. The local distribution of the particles through the fanning out occurs as the particles move in the measuring channel, occurs according to classification of sizes, and is measured by means of a scanning apparatus. For this purpose, outside of the measuring channel in front of one of its radiation permeable side walls, a radiation transmitter is arranged, and in front of the oppositely disposed side wall is arranged a radiation receiver or detector, respectively, correlated with the radiation transmitter, said radiation receiver or detector receiving the measuring beam. Both the radiation transmitter and the radiation receiver are fixed to a forked carrier enclosing the measuring channel, and the measuring unit consisting of a transmitter, receiver, and common carrier, is drivable by a motor along a guide rail transversely to the direction of flow of the measuring channel through a measuring zone extending at least over the width of the material blower. Accordingly, the measuring beam scans the material blower perpendicularly to a plane of fanning-out.

Through the extinction of the radiation, for example, radiation of light or gamma radiation, the particle concentration or particle size distribution is determined within the measuring zone. For the prevention of measuring errors, the radiation transmitter and radiation receiver must in every position always be exactly flush with one another. The inherent frequency of the scanning apparatus, for the prevention of vibrations, must lie very high, somewhat higher than 5 Hertz. This requirement is achieved with known measuring units in the form of a fork only with difficulty and at great expense. The danger exists that during the scanning of the material blower, falsifications in the measuring values can occur which are caused by vibrations in the scanning apparatus or their measuring units.

SUMMARY OF THE INVENTION

It is an object of the invention to provide an apparatus for the determination of the particle size distribution of a granular material, wherein analysis values are not falsified through vibrations of the scanning apparatus and/or its drive.

This object is solved with an apparatus of the type according to the invention wherein the scanning apparatus has a reciprocating measuring frame of closed form carrying the radiation transmitter and the radiation receiver, said measuring frame enclosing the measuring channel with spacing from the same on all sides.

In the apparatus according to the invention, by means of the measuring frame of closed form which may be constructed very resistant to bending, it is insured that the longitudinal struts of the frame on which the radiation transmitter and the radiation receiver flush therewith are fixed, can almost no longer be set into vibrations which would falsify the analysis values determined by the scanning apparatus. Also, the scanning apparatus in this connection and its drive do not have to be of excessively solid and heavy construction for the production of the scanning movement.

According to a further feature of the invention, the measuring frame is hingedly positioned on at least one guide arm and is swingable with the guide arm or arms. The guide arm system, may, for example, consist of three of four guide arms. The guide arms may run in the same direction and may be provided to the same side of the measuring frame. During the horizontal swinging of such a guide arm system, the measuring frame and the radiation transmitter and radiation receiver fixed thereon make a rocking movement, that is, the scanning path of the measuring zone is somewhat arcuate shaped. According to a special feature of the invention, however, the guide arm or the guide arms of one end of the measuring frame go off to one side, and the guide arm or guide arms of the other measuring frame end go off towards the oppositely directed side from the measuring frame. With such a guide arm system, the measuring frame is hingedly supported on one side on guide arms and on the oppositely disposed side is hingedly suspended on at least one guide arm. If, then, according to a further feature of the invention, the radiation transmitter and the radiation receiver are fixed on the longitudinal struts of the measuring frame at a point which lies exactly in the middle between the pivot points of the guide arms of the one measuring frame end and the pivot point of at least one guide arm of the other measuring frame end, the radiation transmitter and the radiation receiver and therefore the scanning measuring beam make an almost horizontal reciprocating movement. In other words, the measuring zone or the scanning path then lies practically horizontally transverse to the measuring channel.

For the horizontal swinging of the measuring frame and therefore the reciprocating movement of the measuring beam, the measuring frame or the guide arm or guide arms, respectively, are hingedly connected at a measuring frame end with a crank rod of a crank drive.

BRIEF DESCRIPTION OF THE DRAWINGS

FIG. 1 shows a view of the scanning apparatus according to the invention for a grain size distribution analyzer; and FIG. 2 is a plan view partially cut away of the apparatus of FIG. 1.

DESCRIPTION OF THE PREFERRED EMBODIMENTS

The measuring channel 10, whose outlines are shown in dash-dot lines in FIG. 2 stands vertically and has a rectangular crosssection. The wide sides 11 and 12 of the measuring channel 10 consist of light permeable glass. The powdered test stream to be analyzed is deposited by means of an injector starting from a narrow side of the measuring channel 10, horizontally into the measuring channel, and is fanned out through a sifting air stream flowing from the top downwardly, according to the grain size. The concentration profile of the fanned out particle stream is scanned by a scanning apparatus. The latter consists of a measuring frame 13 constructed very resistant to bending and of a closed loop construction which surrounds the measuring channel 10 with spacing on all sides. On one longitudinal strut 14 of this measuring frame is fixed a radiation transmitter 15, for example, an illumination lamp. On another longitudinal strut 16 is fixed a radiation receiver 17, for example, a photocell. The diameter of the measuring light beam directed vertically through the measuring channel 10 is about 2 mm.

By means of the emission by lamp 15 of a beam of light whose extinction or absorption, respectively, is measured by means of the photocell 17, the quantitative portions of the individual grain classifications may be determined according to a calibration on the basis of the different extinctions or absorptions, respectively, of the beam of light effected through the material blower in the range of the appropriate particle paths of the particular grain classifications. By means of reciprocating movement of the beam of light over the entire particle concentration profile, the different extinction or absorption, respectively, of the individual zones of the material blower is continuously scanned and confirmed through a corresponding indicating or registering device which is connected with the photocell 17. The evaluation takes place parallel to the measuring, for example, with the aid of an electronic computer.

Since the inherent frequency of the longitudinal struts 14 and 16 of the measuring frame 13 lies very high, these longitudinal struts practically cannot be set into vibration. Therefore, the lamp 15 and the photocell 17 remain always flush with one another so that falsifications of measuring values which would occur through alignment errors of lamp and photocell, are to a large extent prevented.

The measuring frame 13 is supported at one narrow side on guide arms 18 and 19, and on an oppositely disposed narrow side on a guide arm 20. The guide arms 18 and 19 are hingedly supported on bearing blocks 21 and 22, while the guide arm 20 is higedly suspended on the shaft 23 of the bearing blocks 24 and 25. During a horizontal swinging of the measuring frame 13, the joint 26 moves along the circular arc 27 shown in dash-dot lines, and the joint 28 moves along the circular arc 29, shown in dash-dot lines. The radii of both arcs 27 and 29 are equally large. Illuminating lamp 15 and photocell 17 are fixed at one point on the longitudinal struts 14 and 16 of the measuring frame 13 this point lying exactly in the middle of the connecting line 30 between the joints 26 and 28 of the guide arms. With such a guide arm system, the measuring frame 13 during its horizontal swinging and therefore also the scanning light measuring beam, makes an almost horizontal reciprocating movement, that is, the measuring zone or the scanning path 31, shown in dash-dot lines in FIG. 1, then lies practically horizontally transverse to the measuring channel 10.

For the horizontal swinging of the measuring frame 13 and therefore the reciprocating movement of the measuring beam, the guide arm 20 is hingedly connected with the crank-rod 32 of a crank-disk 33 which is driven by a motor 34. In FIG. 1, the measuring frame 13 is located exactly in its reverse position for the movement from left to right. All ball and socket joints are free from play in operation. Thereby the entire measuring frame 13 can practically no longer be set into vibration. The ball and socket bearings are also non-sensitive to dust and can easily be held free from dust. The ball and socket bearings also eliminates the need for an excessively high measuring accuracy for the measuring frame and the guide arm system. The reference character 35 designates the measuring impulse transmitter.

The measuring frame 13 is constructed to be resistant to bending and permits scanning speeds of up to over 40 mm/sec. In all, through the scanning apparatus, an accurate measuring device is furnished which is an advance over previous devices with respect to freedom from measuring errors, velocity, measuring range, solution capacity and reproduceability of the measuring values. With utilization of air as the carrier medium stream, a particle size measuring range of 1 $\mu$m up to at least 200 $\mu$m may be attained.

Although various minor modifications may be suggested by those versed in the art, it should be understood that I wish to embody within the scope of the patent warranted hereon, all such embodiments as reasonably and properly come within the scope of my contribution to the art.

I claim as my invention:

1. A scanning apparatus for the determination of a particle size distribution of a granular material in a measuring channel having radiation permeable side walls and a measuring zone, the granular material being introduced in the measuring channel and distributed according to grain size by a sifting air current, comprising:
   a reciprocating measuring frame having a closed loop portion which surrounds the measuring chamber and with all portions of the loop spaced from the chamber;
   a radiation transmitter means for producing a measuring beam mounted on the measuring frame such that the measuring beam scans the measuring zone of the measuring channel in transverse fashion when the frame is reciprocated in a given manner; and
   a radiation receiver means positioned on the frame and opposite the transmitter means for receiving the measuring beam after it passes through the measuring zone.

2. An apparatus according to claim 1, characterized in that the measuring frame has opposite ends which are each hingedly connected at a joint to at least one guide arm means for reciprocating the frame.

3. An apparatus according to claim 2, characterized in that the measuring frame has opposite sides and that each of the guide arm means extends in a same direction and lie on a same one of the sides.

4. An apparatus according to claim 2, characterized in that the measuring frame has opposite sides and that one of the guide arm means at one of the ends of the measuring frame extends to one of the sides and the guide arm means at the opposite measuring frame end extends to the opposite side of the measuring frame.

5. An apparatus according to claim 2, characterized in that the radiation transmitter means and radiation receiver means are respectively fixed on first and second longitudinal struts of the measuring frame and at a point on each strut which is a center point between the joint of the guide arm means of the one measuring frame end, and the joint of the guide arm means at the other measuring frame end.

6. An apparatus according to claim 2, characterized in that the joints have substantially no play in operation.

7. An apparatus according to claim 1, characterized in that one end of the measuring frame is hingedly connected with a crank member of a crank drive.

8. An apparatus according to claim 1 wherein one of the guide arm means at one of the ends of the frame connects with a crank member of a crank drive.

9. An apparauts according to claim 1 wherein the frame is rectangular and has first and second ends, a first guide arm means connecting to the first end and extending below the frame and a second guide arm means connecting to the second end and extending above the frame, and wherein the measuring beam moves along a substantially horizontal path.

10. A scanning apparatus for the determination of a particle size distribution of granular material, comprising:

a measuring chamber means for distributing granular material according to grain size in a measuring zone of the chamber means;

a measuring frame having a closed loop portion formed of two side walls and end walls within which the measuring zone is positioned;

a radiation transmitter producing a measuring beam being positioned on one of the side walls and a radiation receiver opposite the transmitter being positioned on the other of the side walls, said transmitter being positioned to direct the measuring beam through the measuring zone; and reciprocating means connecting to the measuring frame for causing a back and forth movement of the measuring frame.

11. The apparatus of claim 10 wherein the measuring chamber has a longitudinal dimension and the reciprocating means causes movement of the measuring frame so as to cause transverse scan of the measuring beam with respect to said longitudinal dimension.

* * * * *